(12) United States Patent
Shchervinsky et al.

(10) Patent No.: US 6,324,435 B1
(45) Date of Patent: Nov. 27, 2001

(54) ELECTRICAL CONNECTOR FOR CARDIAC DEVICES

(75) Inventors: Semyon Shchervinsky, Whitehouse Station; Lowell Saferstein, West Orange; Alex B. Ilori, Flemington; Robert E. Maurer, Belle Mead, all of NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/599,197

(22) Filed: Jun. 22, 2000

(51) Int. Cl.$^7$ .................................................. A61N 1/05
(52) U.S. Cl. .............................. 607/152; 600/374
(58) Field of Search ................................. 607/129, 142, 607/152; 600/374

(56) References Cited

U.S. PATENT DOCUMENTS

| | | | |
|---|---|---|---|
| 3,650,276 | 3/1972 | Burghele et al. ............ | 128/419 E |
| 3,724,467 | 4/1973 | Avery et al. .................. | 128/418 |
| 4,057,067 | 11/1977 | Lajos ............................ | 128/418 |
| 4,144,889 | 3/1979 | Tyers et al. .................. | 128/418 |
| 4,323,081 | 4/1982 | Wiebusch ..................... | 128/785 |
| 4,553,554 | 11/1985 | Lemole ........................ | 128/784 |
| 4,899,754 | * 2/1990 | Bly et al. . | |
| 5,341,806 | 8/1994 | Gadsby et al. ............... | 128/640 |
| 5,527,358 | 6/1996 | Mehmanesh et al. ........ | 607/129 |
| 6,038,464 | * 3/2000 | Axelgaard et al. . | |
| 6,038,485 | * 3/2000 | Axelgaard . | |

* cited by examiner

*Primary Examiner*—Scott M. Getzow
(74) *Attorney, Agent, or Firm*—Matthew S. Goodwin (57) ABSTRACT

An electrical connector for a cardiac device is disclosed. The connector has a wire and an electrode at the distal end of the wire. The wire is attached to a patch, and the patch is coated with an adhesive film for adhering the patch to tissue. The preferred connector is a bipolar temporary cardiac pacing wire. The use of an adhesive film eliminates or reduces the need for suturing the patch to tissue, thus avoiding or significantly reducing tissue trauma associated with suturing.

16 Claims, 7 Drawing Sheets

ELECTRICAL CONNECTOR FOR CARDIAC DEVICES

FIELD OF THE INVENTION

The present invention relates to electrical connections for cardiac devices and, more particularly, to temporary cardiac pacing wires that are adapted for use with apparatus that generate electrical signals suitable for stimulating, pacing, sensing, monitoring or defibrillating the heart.

BACKGROUND OF THE INVENTION

Devices to stimulate or regulate cardiac function have been known and used for decades. They involve a power source (pacemaker) and one or more surgical electrodes to attach the source to the heart. They are generally of two types.

Implantable pacers are intended for long-term use and, as the name suggests, are entirely implanted in the body. The other type is intended for temporary use. The temporary pacemaker is located outside the body and is connected to the heart by a surgical electrode called a "temporary pacing wire." Although surgical electrodes are used for preparing electrocardiograms and other applications, for the sake of brevity, the description that follows is focused on temporary pacing wires.

In general, such wires are constructed of a number of fine stainless steel wires braided or twisted together to form a single, flexible, multi-strand electrode wire. The major portion of the wire is electrically insulated with a polyethylene, polytetrafluoroethylene, silicon, nylon, or another non-conducting coating, with a short length of wire at either end left uninsulated. With respect to the conventional temporary pacing wires, to the distal uninsulated end of the electrode wire there is attached, by swaging or other means, a fine curved needle for piercing the heart tissue to place the uninsulated end of the electrode in the myocardium. At the proximal end of the electrode wire, a straight (e.g., Keith-type) cutting needle is attached for piercing the thoracic wall to lead the electrode to an outer point for connection with the pacemaker. Once that has been accomplished, the needle or its sharp-pointed end is clipped or broken and the proximal end of the electrode is readied for attachment to the pacemaker as required to stimulate or regulate the beating of the heart. A single setup involves two electrodes, i.e., two temporary pacing wires.

During the time that the temporary pacing wire is performing its function, the uninsulated end of the electrode must remain anchored in the myocardium. The anchorage of the uninsulated end of the electrode to the myocardium must be secure, lest the continually beating heart cause the wire to be expelled from the myocardium. Conventionally, the electrode is sutured directly to the myocardium, or it is attached to a pad which in turn is sutured to the myocardium. Suturing causes trauma to the heart tissue. Additionally, when the need for the pacing wire has passed, it is necessary to remove from the body the wire that runs from the external pacemaker to the myocardium. The removal of the sutured wire can also cause trauma.

DESCRIPTION OF THE RELATED ART

U.S. Pat. No. 5,527,358 discloses a temporary medical electrical lead having a pad that contains holes which expose conductive sections of electrode wires to cardiac tissue in a discontinuous fashion. The pad is permanently implanted on the atrial wall and remains implanted after removal of the temporary electrodes. The conductors are mounted to the pad. Means disclosed for attaching the conductors to the pad include suturing or gluing all or some of the conductors to an outer surface of the mounting pad. The holes within the pad are used to provide for windows for the conductors to be exposed to body tissue (e.g., cardiac tissue). Bus are placed at the proximal end of the pad to prevent the conductors from accidentally dislodging while also allowing their intentional dislodgment and removal without excessive forces after treatment. Unfortunately, the pad is sutured to the atrial wall and this causes trauma. Additionally, the pad remains attached to the atrial wall even after the electrode wires are removed.

U.S. Pat. Nos. 4,553,554; 4,144,889; 3,724,467; 5,341,806; 4,057,067; 3,650,276 and 4,323,081 disclose similar pacing leads and surgical electrodes for cardiac and other surgical applications. All of these describe suturing or other mechanical means to attach the electrodes to tissue, consequently leading to undesirable trauma to the surgical patient.

Copending and commonly assigned U.S. application Ser. No. 09/451,590, filed on Nov. 30, 1999, and Ser. No. 09/451,591 filed Nov. 30, 1999, also describe electrical connectors for cardiac devices. The electrode wires are sutured to the myocardium.

In view of the inherent difficulties as described in the foregoing, there is a need for an electrical connector for a cardiac device, particularly a temporary pacing wire, where the electrode can be attached to the tissue of the patient without the unwanted trauma which occurs when the electrodes or pads to which the electrodes are attached are sutured into the cardiac tissue. Additionally, it would be desirable if all of the components of the electrical connector, including any pad which is used for mounting of the electrode, can be completely and easily removed from the patient after the connector is used.

SUMMARY OF THE INVENTION

The invention is an electrical connector for a cardiac device. The connector comprises a wire having a distal end, a first electrode at the distal end of the wire, and a patch at the distal end of the wire. The patch has an external surface and a tissue-contacting surface. The tissue-contacting surface of the patch is coated with an adhesive film for adhering the patch to the targeted tissue. The electrode is in contact with the adhesive film coated on the tissue-contacting surface of the patch.

The adhesive film applied to the tissue-contacting surface of the patch provides a sufficient bond between the patch and a targeted tissue surface. This bond is significant because it provides a reliable attachment of the electrode at the distal end of the wire of the electrical connector to the tissue surface. Significantly, the attachment of the electrode to the tissue surface can be accomplished in the most preferred embodiments of this invention without any need to suture the patch to the targeted tissue surface. Consequently, the trauma associated with the suturing of sensitive bodily tissue can be avoided or at the very least minimized.

Additionally, not only can the wire be readily removed from the patient after use, but also the patch can be easily removed from the patient as well. In this manner, it is unnecessary to leave any components of the electrical connector in the patient's body permanently, in contrast to those connectors which require suturing for the attachment of the pad to the targeted tissue surface.

The electrical connector of this invention can be used in any surgical procedure where an electrical signal in a cardiac application is required.

DETAILED DESCRIPTION OF THE PREFERRED EMBODIMENT

Although the present invention is applicable to many different types of cardiac devices, including monopolar and quatropolar devices, it is especially suitable for use in conjunction with a bipolar temporary cardiac pacing wire. Accordingly, the present invention will be described below in connection with such a pacing wire.

As used herein, the term "distal" shall mean that portion of the pacing wire or element thereof which is remote from a source of electric signals located external to the patient's body. Conversely, the term "proximal" shall mean that portion of the pacing wire or element thereof which is in close proximity to the external source of electrical signals.

Figure 1:
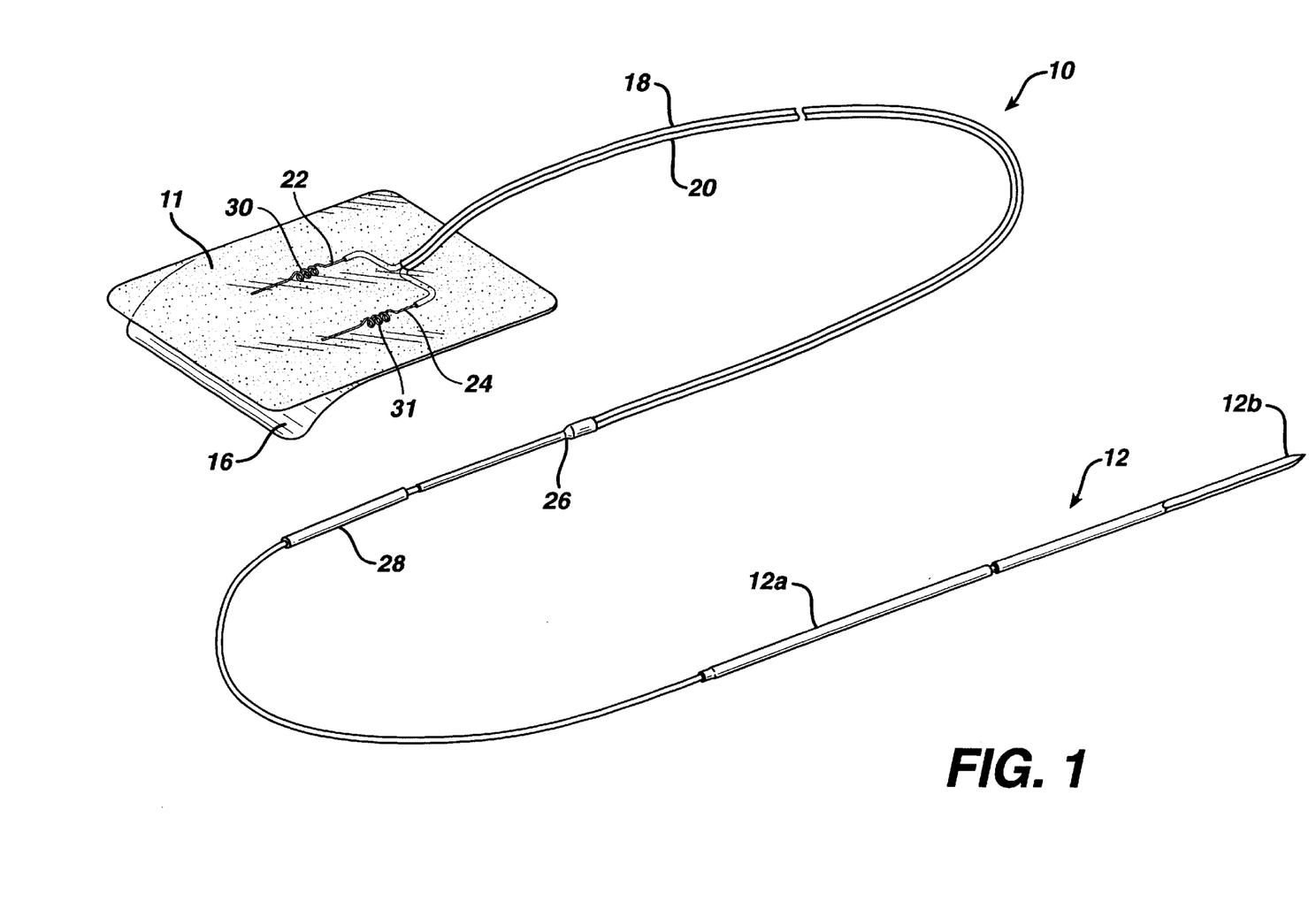
FIG. 1 is a perspective view of the most preferred electrical connector of this invention, which is a bipolar temporary cardiac pacing wire.

Referring initially to FIG. 1, a bipolar temporary cardiac pacing wire 10 includes a Keith-type breakaway needle 12 arranged at a proximal end of the pacing wire 10. The Keith-type needle 12, such as the one disclosed in U.S. Pat. No. 4,010,756 issued on Mar. 8, 1977 to DuMont et al., has a distal section 12a and a proximal section 12b, which is pointed for piercing the thoracic wall to lead the proximal end of the pacing wire 10 outside the chest cavity of a patient in accordance with a medical procedure well known in this field. At the distal end of the pacing wire 10 there are first and second electrodes 22, 24. The electrodes are affixed to a patch 11, which will be described in more detail below.

A pair of insulated, electrical conductive electrode wires 18, 20 extends between the distal and proximal ends of the pacing wire 10. The electrode wires 18, 20 are of the "lamp cord" type (i.e., they are arranged in a side-by-side fashion as shown in FIG. 1) where each wire has a braided, multi-stand core of stainless steel and a surrounding layer of insulation made from polyethylene. The core of each wire could have a twisted construction with a surrounding layer of insulation made from polyethylene or any other suitable electrical non-conducting material, such as silicon, polytetrafluoroethylene, or nylon.

The electrode 22 is electrically connected to the electrode wire 18, and the electrode 24 is electrically connected to the electrode wire 20. The electrodes 22, 24 have a conventional construction and are adapted to transmit electrical signals from one to the other for the purpose of stimulating, pacing, sensing, monitoring, or defibrillating the heart. Alternatively, the electrodes 22,24 can be composed of a "smart" metal, or a shape memory alloy, preferably Nitinol alloy.

At the proximal end of the pacing wire 10 there are two connectors 26, 28. The connector 26 is mechanically and electrically connected to the electrode wire 20, but only mechanically connected to the electrode wire 18. Electrode wire 18 passes through the elongated, sleeve-like connector 26 and is mechanically and electrically connected to the Keith-type needle 12 in a conventional manner. The other elongated, sleeve-like connector 28 is positioned on the electrode wire 18 intermediate to the connector 26 and the Keith-type needle 12. Unlike the connector 26, which is electrically connected to the electrode wire 20, the connector 28 does not have to be electrically connected to either of the electrode wires 18, 20. However, the connector 28 may be electrically connected to the electrode wire 20, which could also be electrically connected to both of the connectors 26, 28. Each of the connectors 26, 28 extends circumferentially about the electrode wire 18 and is made from suitable electrically conductive material, such as stainless steel. While the connectors 26, 28 have a generally circular cross-sectional shape, they could have other cross-sectional shapes, such as oval, square, rectangular, etc.

The patch 11 is preferably a flat, polymeric film. It can be bioabsorbable or non-bioabsorbable. The patch desirably exhibits elasticity and flexibility to readily conform to a beating heart surface. In addition, the patch may have perforations to aid in conformity and adherence to the heart surface. The patch may be of a knitted construction, or a woven or non-woven construction, or any other textile fabric construction. Alternatively, it can be a sponge, or a composite of several bioabsorbable or non-bioabsorbable materials. The patch is preferably a polymeric film which is gas and moisture permeable. Preferably, the patch is a polymeric film composed of poly (p-dioxanone).

Figure 4:
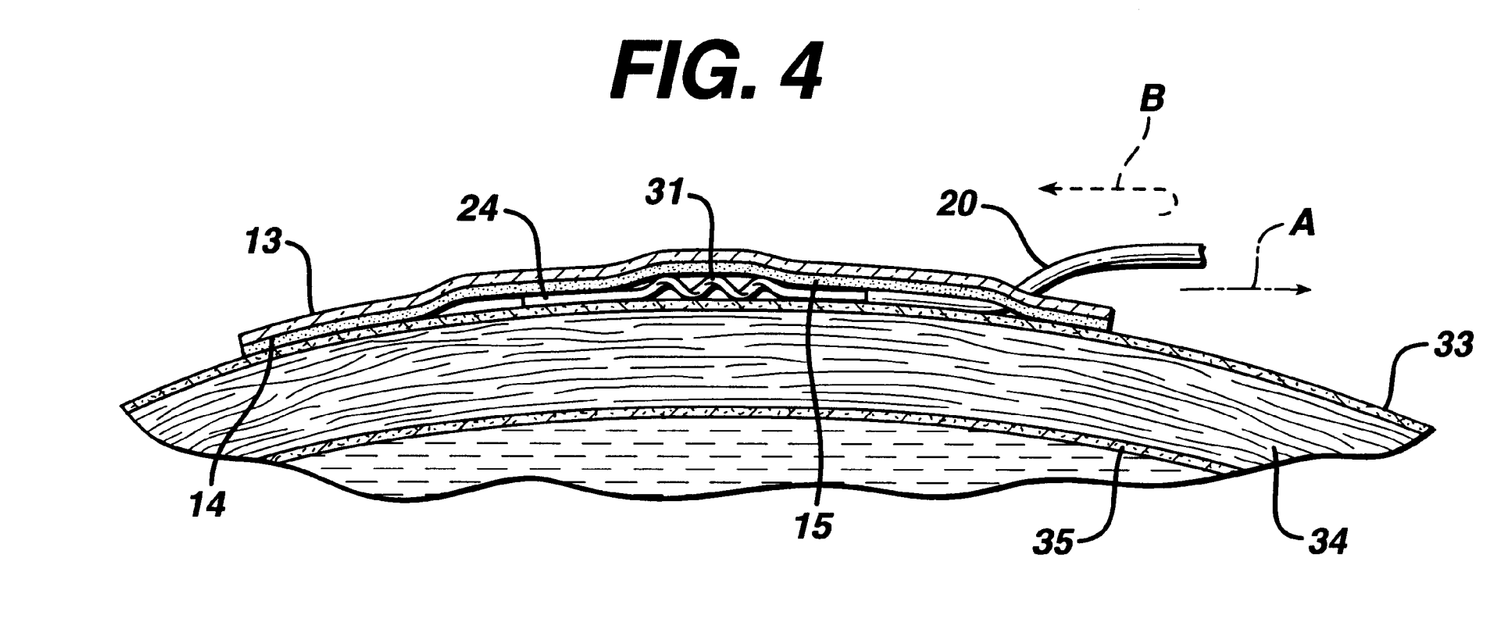
FIG. 4 is a cross-sectional view taken along line 4—4 of FIG. 3.

Referring to FIG. 4, the patch has an external surface 13 and a tissue-contacting surface 14. The tissue-contacting surface is coated with an adhesive film 15. Suitable adhesive compositions include, but are not limited to, bovine albumin and glutaraldhyde, polyethylene glycol, collagen pellets, thrombin, protein polymers, tacky gelatin adhesive, hydrocolloidal butyl base adhesive, and silicone adhesive. The adhesive may also be be composed of a moisture activated polymeric film such as, for example, a polyvinyl alcohol film. The preferred adhesive film is a pressure sensitive medical grade adhesive. The most preferred adhesive is a medical grade silicone adhesive, particularly RTV silicone adhesive.

Figure 2:
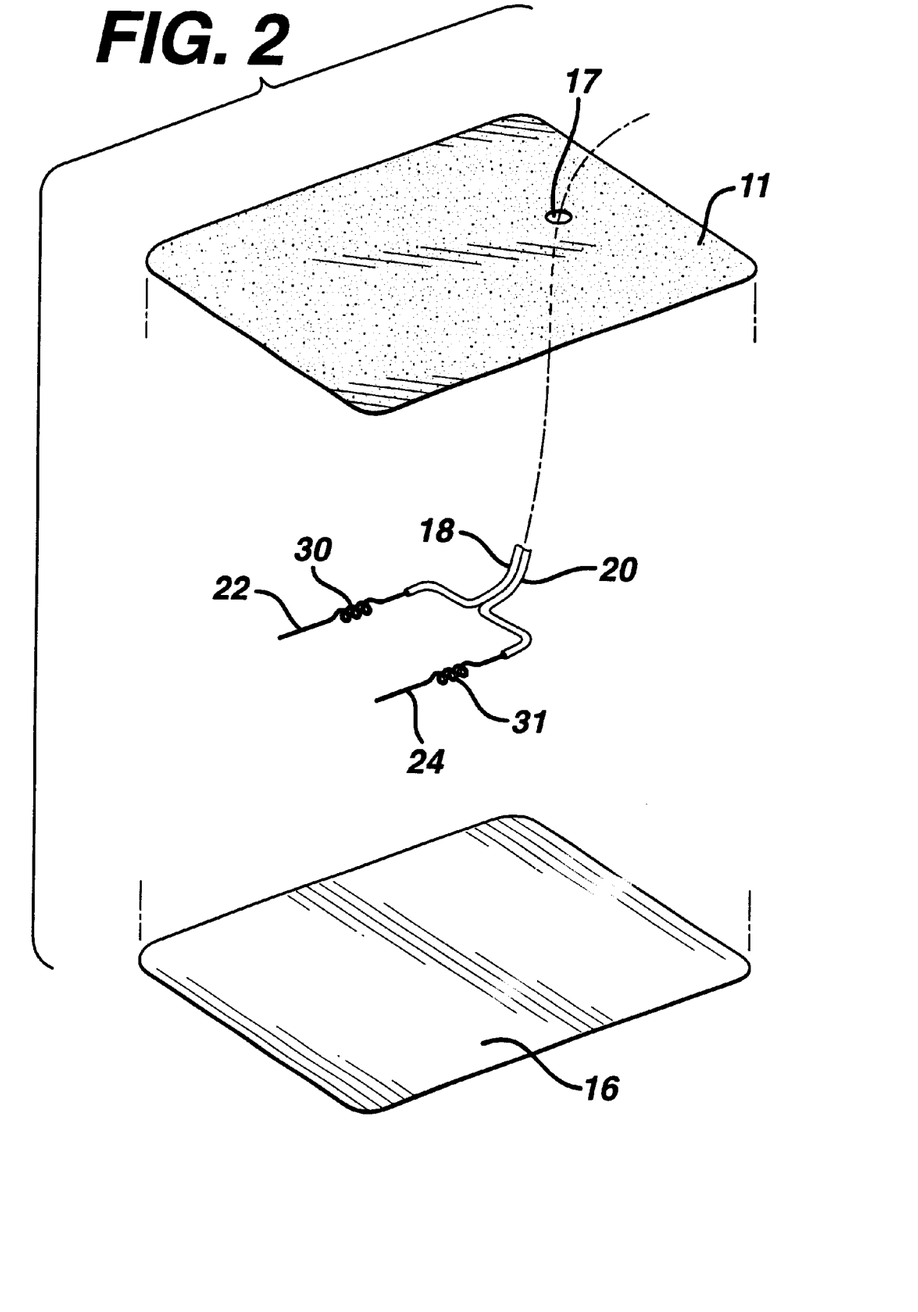
FIG. 2 is an exploded perspective view of the distal end of the pacing wire of FIG. 1.
Figure 3:
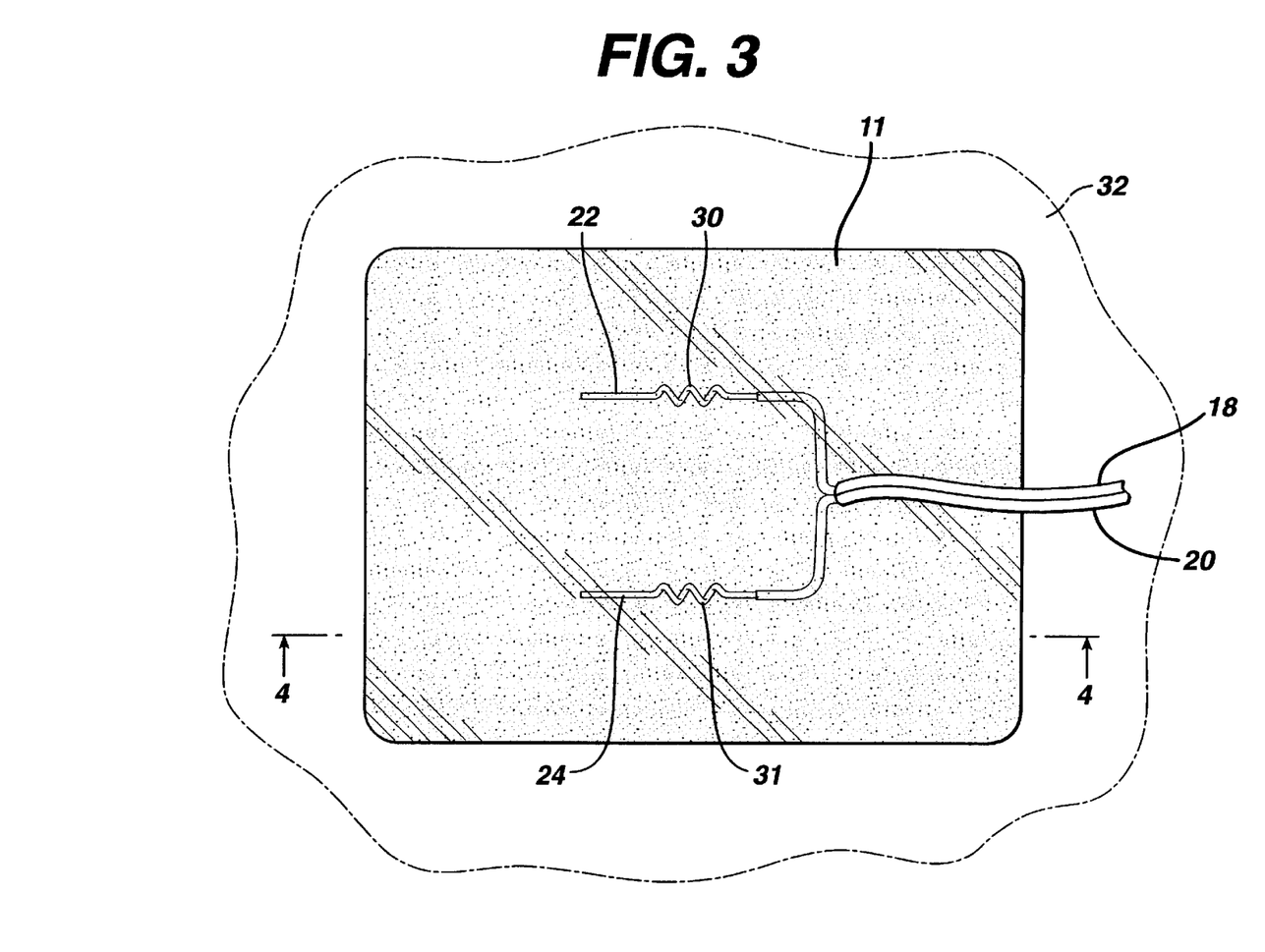
FIG. 3 is a top plan view of the distal end of the bipolar wire of FIG. 1, illustrating the attachment of the patch to the heart wall of the patient.

Referring again to FIG. 1 in combination with FIGS. 2–4, the first and second electrodes 22, 24 are L-shaped electrodes which are fixed to the tissue-contacting surface 14 of the patch 11. Affixing of the electrode to the patch is accomplished when the electrodes are adhered to the adhesive film 15 coated on the tissue-contacting surface of the patch. The electrode wires 18, 20 of the bipolar pacing wire 10 are received through a hole 17 in the patch. The wires are bent or curved at the portion passing through hole 17. This works to further secure the wires to the patch in combination with the adhesive film. In order to cover the tissue-contacting surface of the patch which contains the adhesive film, a release paper 16 is attached to the adhesive film for proper storage, handling and use.

In the most preferred embodiment, each of the first and second L-shaped electrodes 22, 24 has a spiral portion 30, 31 to increase the surface area of the electrodes exposed to the heart tissue and enhance the bonding of the electrodes to the tissue as a result of the adhesive film.

Figure 5:
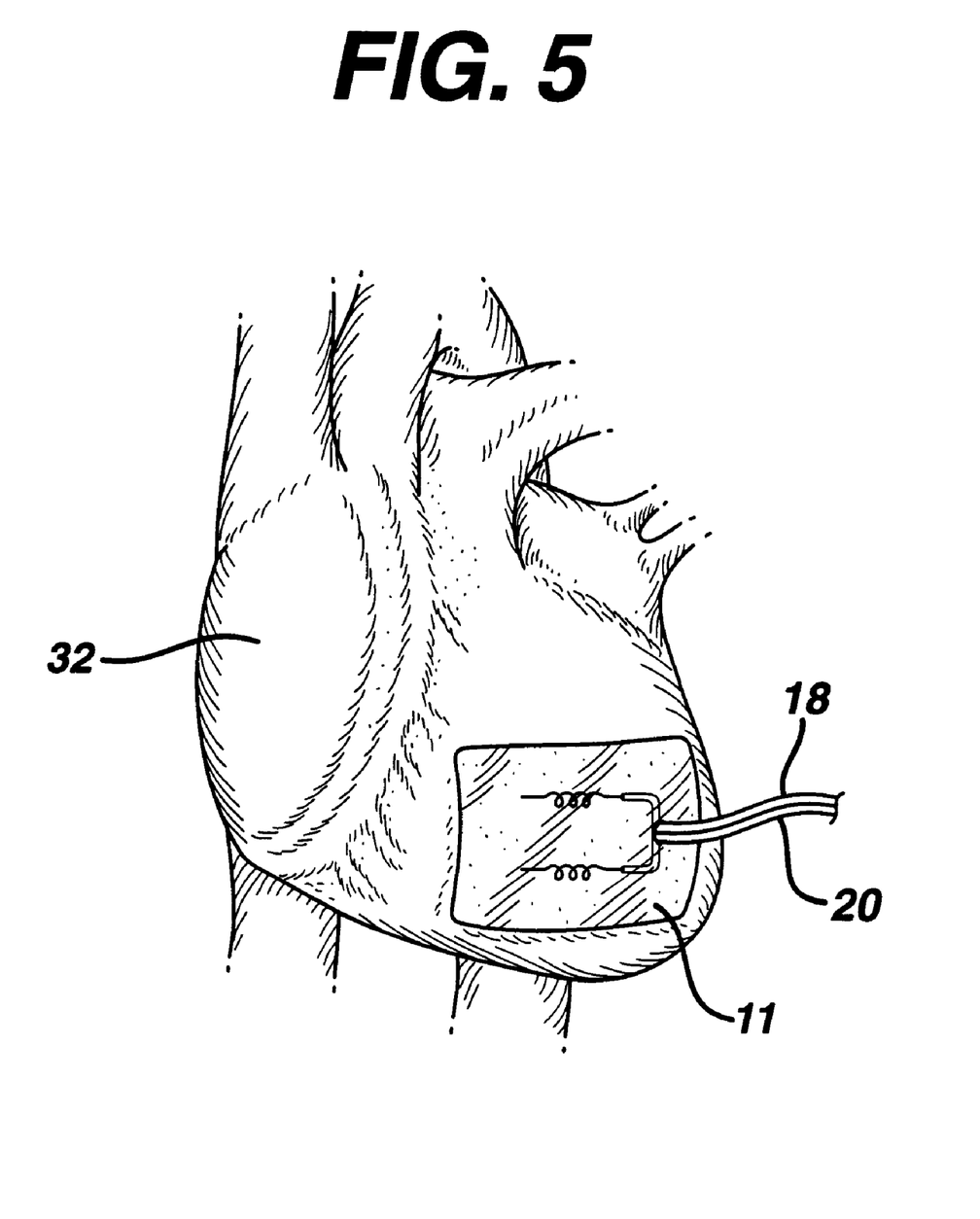
FIG. 5 is a perspective view of the distal end of the bipolar wire of FIG. 1 affixed to the heart.
Figure 6:
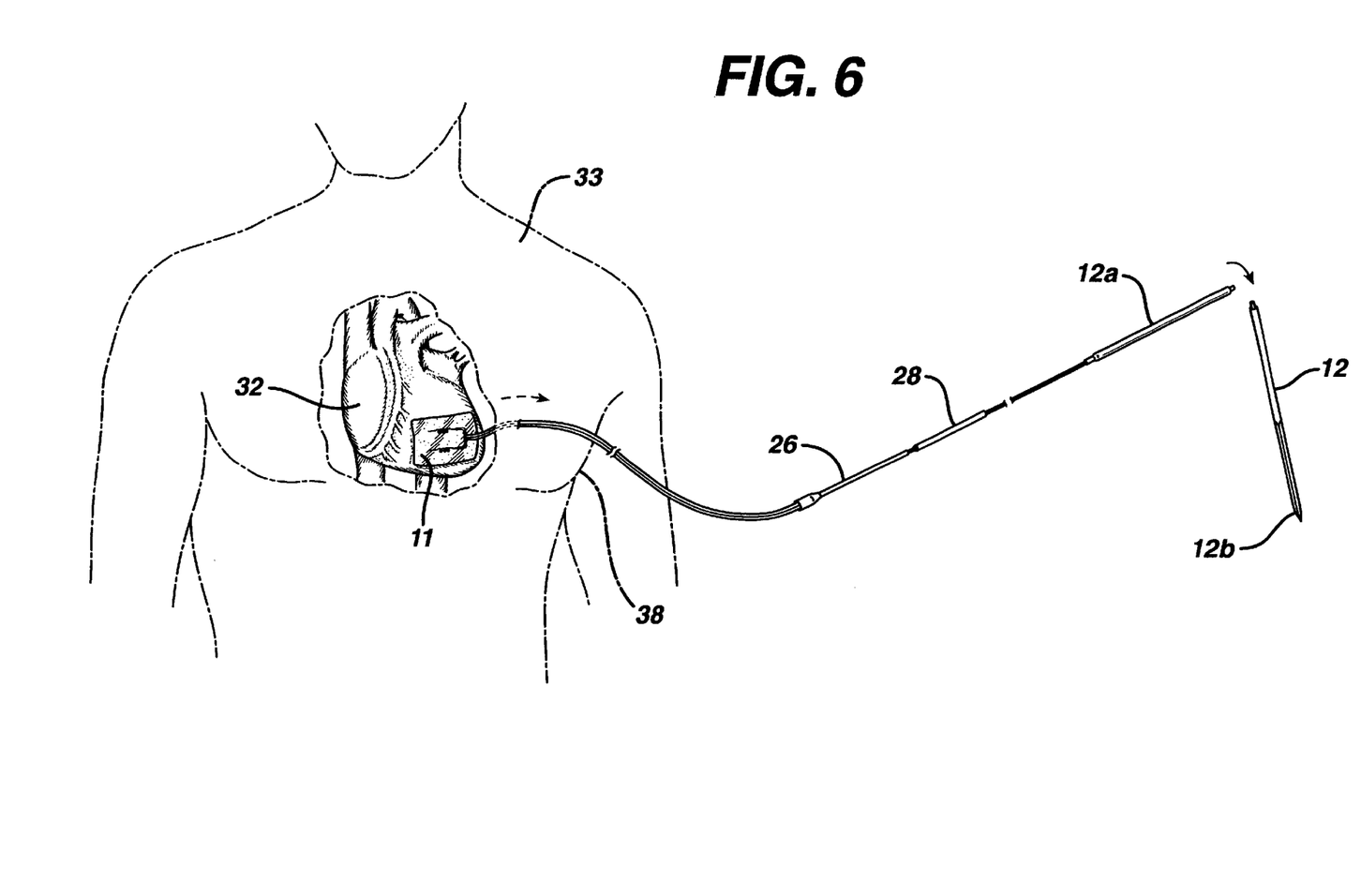
FIG. 6 is a perspective view illustrating the placement of the bipolar wire of FIG. 1 onto the heart.
Figure 7:
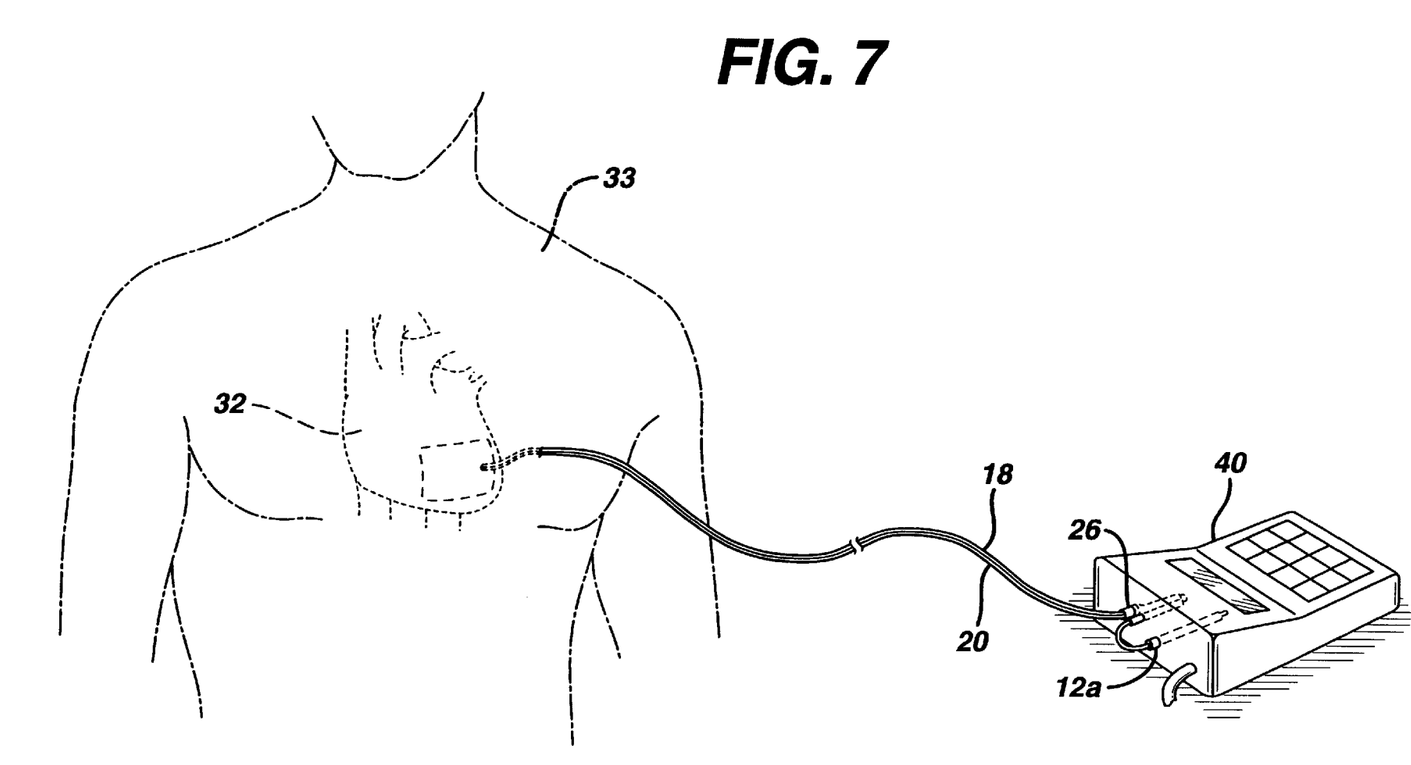
FIG. 7 is a perspective view of the bipolar wire of FIG. 1 illustrating the attachment of the bipolar connectors at the proximal end of the wire into a pacemaker.

When the surgeon wishes to apply the preferred bipolar temporary pacing wire, he attaches the patch 11 carrying the exposed electrodes to the heart 32 of the surgical patient 33 (see FIGS. 5–7). To do this, he removes the release paper 16, thus exposing the adhesive film 15 on the tissue-contacting surface 14 of the patch.

With the application of pressure, the patch can be adhered to the heart. As illustrated in FIGS. 3–5, once pressure is applied, the exposed first and second L-shaped electrodes 22, 24 are positioned into electrical contact with the heart surface 33. The adhesive film on the tissue-contacting surface of the patch assures an adequate bond between the patch and the heart surface, thus insuring that the exposed electrodes attached to the heart surface will not be dislodged during use of the bipolar temporary pacing wire. Also illustrated in FIG. 4, there is shown the myocardium 34 and endocardium 35 of the heart.

FIG. 4 nicely shows the protrusion of the insulated electrode wires through the hole 17 of the patch. Turning now to FIG. 6, the Keith-type needle is used to pierce the thoracic wall 38 of the patient. Once the bipolar wire protrudes from the patient, the needle 12 is severed at distal section 12a to expose the connector 28. As illustrated in FIG. 7, the connectors 26, 28 are inserted into the sockets of a pacemaker 40. For a more detailed explanation of the connection between the connectors and the pacemaker, the reader is referred to co-pending and commonly assigned U.S. application Ser. No. 09/451,590, filed Nov. 30, 1999.

Once the temporary pacing is completed, the bipolar wire is removed from the patient. As illustrated in FIG. 4, the insulated electrode wires and patch can simply be pulled in the direction of directional arrow "A" at a 0° angle with respect to the surface of the heart surface 33. Alternatively, if desired, the wires and patch can be pulled in the direction of directional arrow "B" at an angle of 180° to remove the wire. The direction of pulling will be pre-determined based on the orientation of the patch with respect to the path the electrodes take to exit the body cavity. This is determined during implantation.

The following Example illustrates the application of the preferred temporary pacing wire of this invention. This example is intended to be illustative only, and it is not intended to limit the scope or spirit of the invention, which is defined in the claims which appear below. Numerous additional embodiments will become readily apparent to those skilled in this art.

EXAMPLE

Bipolar temporary pacing wires were constructed in accordance with the preferred embodiment of this invention and as illustrated in the figures. The wires were applied to wet pig hearts. The patches used for affixing the electrodes to the heart were composed of poly (p-dioxanone) polymer films coated with pressure sensitive medical grade RTV silicone adhesive. Each patch was about two square inches in size. 7 mg/in.sq. of adhesive was applied from the adhesive tube directly onto the tissue-contacting surface of each film. The first and second electrodes of the pacing wire were then affixed to the tissue-contacting surface of the polymeric film. Alternatively, any pressure sensitive adhesive could have been pre-applied to the film and subsequently covered by a release paper such as silicone paper.

A Chatillon Tensile Tester (crosshead speed=12 in/min with force gauge DFSI-50) was clamped onto a free portion of the proximal end of the pacing wire. The pacing wire was then removed. Results showed an average pullout force of 70 gm., with a standard deviation of 10 gm. These values were comparable to those generated with commercially available pacing wire.

Measurements were then made to obtain the force required to remove the two square inch polymer film from the wet heart surface. These measurements resulted in a pullout force of 150 gm., with a standard deviation of 20 gm., demonstrating that the polymeric film could be removed from the heart without excessive trauma.

What is claimed is:

1. An electrical connector for a cardiac device, said connector comprising:
    a) a wire having a proximal end and a distal end,
    b) a first electrode at the distal end of said wire,
    c) a patch at the distal end of said wire, said patch having an external surface and a tissue contacting surface, said tissue contacting surface of said patch being coated with an adhesive film for adhering said patch to tissue, and said electrode being in contact with said adhesive film coated on said tissue contacting surface of said patch, and
    d) a breakaway needle attached to the proximal end of said wire.

2. The connector of claim 1 wherein said patch is a polymeric film.

3. The connector of claim 2 wherein said polymeric film is bioabsorbable.

4. The connector of claim 2 wherein said adhesive film is a pressure sensitive medical grade adhesive.

5. The connector of claim 4 wherein said adhesive is a medical grade silicone adhesive.

6. The connector of claim 2 wherein said patch has a release paper attached to said adhesive film on said tissue contacting surface for exposing said adhesive film upon release of said paper.

7. The connector of claim 1 wherein said breakaway needle is a Keith-type needle.

8. The connector of claim 1 wherein said connector is a bipolar temporary cardiac pacing wire.

9. The connector of claim 8 wherein said pacing wire has a pair of insulated, electrically conductive electrode wires extending between the proximal and distal ends of said pacing wire.

10. The connector of claim 1 wherein said patch has a hole therein.

11. The connector of claim 10 wherein said electrode wires are received through said hole in said patch.

12. The connector of claim 11 wherein said pacing wire further comprises a second electrode at the distal end of said wire.

13. The connector of claim 12 wherein said first and second electrodes are L-shaped electrodes.

14. The connector of claim 13 wherein each of said first and second electrodes has a spiral portion.

15. The connector of claim 1 wherein said first and second electrodes are composed of a shape memory alloy.

16. The connector of claim 15 wherein said shape memory alloy is a Nitinol alloy.

* * * * *